(12) United States Patent
Simske et al.

(10) Patent No.: US 7,962,201 B2
(45) Date of Patent: Jun. 14, 2011

(54) METHODS OF GENERATING A VIRTUAL LEAD ASSOCIATED WITH A PHYSIOLOGICAL RECORDING

(75) Inventors: Steven J. Simske, Fort Collins, CO (US); Daniel Robert Blakley, Philomath, OR (US); Tong Zhang, San Jose, CA (US)

(73) Assignee: Hewlett Packard Development Company, L.P., Houston, TX (US)

( * ) Notice: Subject to any disclaimer, the term of this patent is extended or adjusted under 35 U.S.C. 154(b) by 336 days.

(21) Appl. No.: 11/221,562

(22) Filed: Sep. 7, 2005

(65) Prior Publication Data

US 2006/0235322 A1 Oct. 19, 2006

Related U.S. Application Data

(63) Continuation-in-part of application No. 11/107,264, filed on Apr. 15, 2005.

(51) Int. Cl.
*A61B 5/0402* (2006.01)
(52) U.S. Cl. ...................................... 600/509
(58) Field of Classification Search .................. 600/512, 600/509, 523–525
See application file for complete search history.

(56) References Cited

U.S. PATENT DOCUMENTS

| | | | |
|---|---|---|---|
| 4,136,690 A * | 1/1979 | Anderson et al. | 600/512 |
| 5,259,387 A | 11/1993 | dePinto | |
| 5,469,856 A | 11/1995 | Lundstrom et al. | |
| 5,690,118 A | 11/1997 | Sornmo et al. | |
| 5,704,365 A | 1/1998 | Albrecht et al. | |
| 5,713,367 A * | 2/1998 | Arnold et al. | 600/517 |
| 5,924,980 A | 7/1999 | Coetzee | |
| 6,052,615 A * | 4/2000 | Feild et al. | 600/509 |
| 6,505,067 B1 * | 1/2003 | Lee et al. | 600/509 |
| 6,658,284 B1 | 12/2003 | Rosen et al. | |
| 6,804,550 B1 * | 10/2004 | Murray | 600/509 |
| 6,856,831 B2 * | 2/2005 | Griffin et al. | 600/515 |
| 6,901,285 B2 * | 5/2005 | Schreck | 600/509 |
| 7,266,408 B2 * | 9/2007 | Bojovic et al. | 600/512 |
| 2003/0083587 A1 * | 5/2003 | Ferek-Petric | 600/512 |

FOREIGN PATENT DOCUMENTS

| | | |
|---|---|---|
| GB | 2 342 449 | 12/2000 |
| WO | WO 2004/089210 | 10/2004 |

OTHER PUBLICATIONS

Ask; "ECG Electrodes, A Study of Electrical and Mechanical Long-term Properties"; Depts of Biomedical Eng & Dermatology, Sweden, Acta anaesth.scand. 1979, 23, pp. 189-206.

* cited by examiner

*Primary Examiner* — Scott M Getzow
*Assistant Examiner* — Amanda Patton

(57) ABSTRACT

A method of creating a virtual lead associated with a physiological recording is provided. The method can include obtaining a first physiological signal from a first lead having a first angle and a second physiological signal from a second lead having a second angle, the first lead and the second lead being associated with a subject. The method can also include transforming the first and second physiological signals into a vector representation of the first and second physiological signals and transforming the vector representation to a virtual physiological signal representing a virtual lead having a virtual lead angle.

23 Claims, 1 Drawing Sheet

METHODS OF GENERATING A VIRTUAL LEAD ASSOCIATED WITH A PHYSIOLOGICAL RECORDING

PRIORITY DATA

This application is a continuation-in-part of U.S. patent application Ser. No. 11/107,264, filed on Apr. 15, 2005, which is incorporated herein by reference in its entirety.

BACKGROUND OF THE INVENTION

The recording and analysis of various types of physiological signals often facilitate the diagnosis and treatment of many medical conditions. These signals can be obtained by measuring a difference in electrical potential between at least two electrodes placed at different points on or near the body. The location of these electrodes defines a recording angle that may influence the observable characteristics of the physiological signal. Because of this, as the relative locations of the electrodes change, the characteristics of the recorded physiological signals may change as well.

In order to diagnose and treat many types of medical conditions, medical professionals look for specific characteristics of physiological signals that are indicative of such conditions. This process may be complicated by changes in the characteristics of the physiological signals due to variations in the recording locations on a subject, or variations in recording quality. Such variations may be due to skin irritation, desiccation of an electrode, defoliation of the skin, etc. Patients may also need to remove and reattach electrodes for a variety of reasons, which tend to cause variations in the recording locations. As such, medical professionals acquainted with physiological signals of a specific angle from a particular subject may have difficulty analyzing the altered physiological signals in relation to the prior signals. Such difficulty can lead to a higher incidence of diagnosis and treatment mistakes.

One example of a physiological signal that is commonly recorded is an electrocardiogram (ECG). ECG recordings are important indicators used in the diagnosis and/or treatment of many cardiac abnormalities and diseases. The ECG is a graphical representation of the electrical voltage in the heart produced during a cyclical heartbeat. In present clinical practice, up to 12 leads are often employed simultaneously for ECG monitoring. One common ECG method utilizes three leads; Lead I, Lead II, and Lead III. Each lead has a negative and a positive electrode that measure electrical potentials between various points on the body. Typically, Lead I measures the electrical potential from the right arm to the left arm, Lead II measures the electrical potential from the right arm to the left leg, and Lead III measures the electrical potential from the left arm to the left leg. From this, three additional "augmented" leads, $aV_R$, $aV_L$, and $aV_F$, measure electrical potentials between a point V located centrally in the chest and each of the three limb leads.

ECG leads measure the average electrical activity generated by the summation of the action potentials of the heart at a particular moment in time. For example, during normal atrial systole, the summation of the electrical activity produces an electrical vector that is directed from the sinoatrial (SA) node towards the atrioventricular (AV) node, and spreads from the right atrium to the left atrium. This directionality is a result of the location of the SA node in the right atrium. This electrical activity is represented by the P wave of the ECG.

Given the importance of ECGs and other physiological signals in the diagnosis and treatment of many medical conditions, inconsistencies in the appearance of such signals over time may impede the diagnosis and/or treatment of a subject.

DETAILED DESCRIPTION OF THE PREFERRED EMBODIMENT(S)

Figure 1:
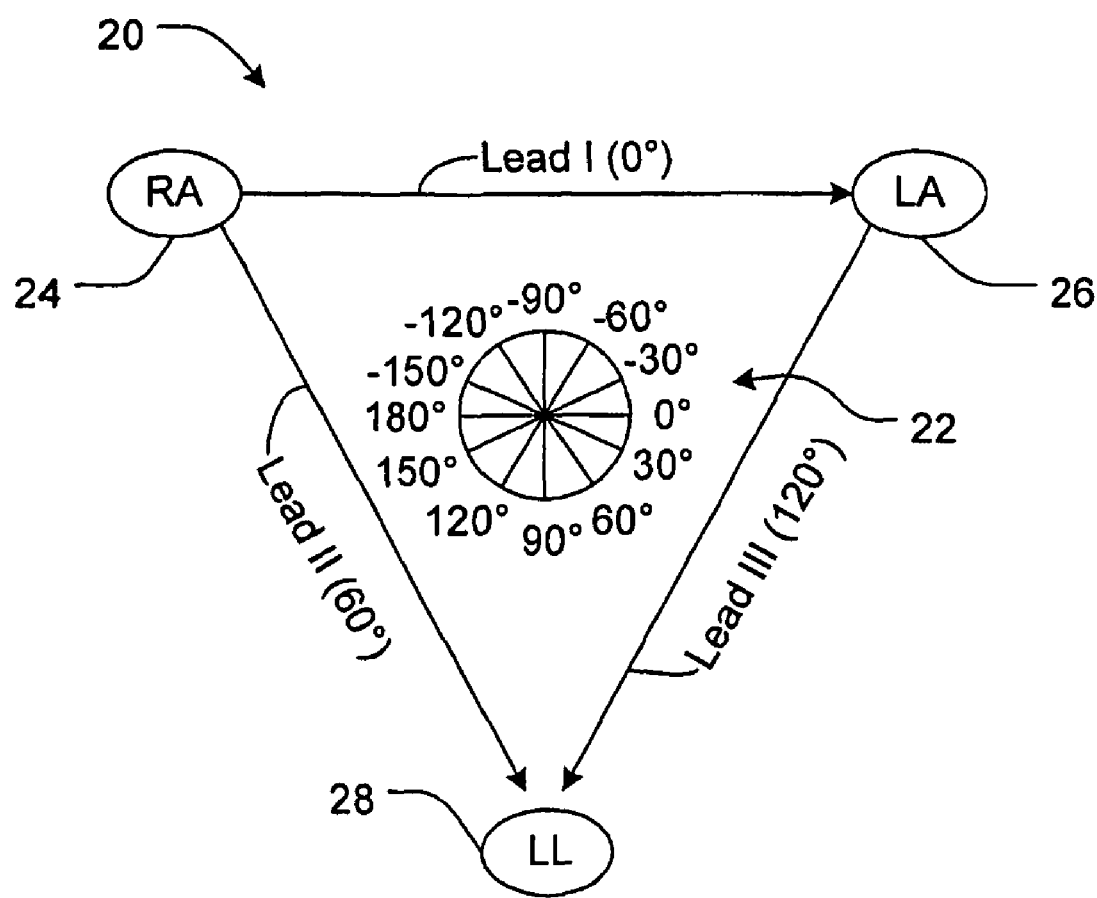
FIG. 1 is a graphical representation of a three-lead electrocardiogram configuration in accordance with an embodiment of the present invention.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a variable" includes reference to one or more of such variables.

The term "physiological signal" refers to a recording or measurement derived from electrical activity generated by a physiological process.

As used herein, "electrocardiogram", "EKG" and "ECG" can be used interchangeably, and refer to recordings of electrical activity associated with the heart.

As used herein, "vectorcardiogram" and "VCG" can be used interchangeably, and refer to a representation of the magnitude and direction of the electrical activity associated with the heart in the form of vector loops.

The terms "electroencephalogram" and "EEG" can be used interchangeably, and refer to recordings of electrical activity associated with the brain.

The terms "electromyogram" and "EMG" can be used interchangeably, and refer to recordings of electrical activity associated with striated muscle.

As used herein, "a lead" refers to a pair of electrodes utilized to measure the electrical potential between two locations. In one aspect, the two locations may be on or near the body of a subject.

As used herein, "signal" and "waveform" may be used interchangeably, and refer to a representation of the flow of information through a lead. It is also intended that these terms include a representation, graphical or otherwise, of single and/or multiple physiological signals, for example, a single ECG, VCG, EMG, or EEG, or multiple ECGs, VCGs, EMGs, or EEGs.

As used herein, "signal artifact" and "noise artifact" may be used interchangeably, and refer to undesirable signal contamination that may or may not obscure information content of a physiological signal.

As used herein, the term "vector representation" refers to a representation of the magnitude and direction of the electrical activity associated with a physiological system in the form of vector loops.

The term "virtual" as used herein refers to any transformation that occurs via a VCG. For example, an ECG signal that is transformed to a VCG and then back to an ECG would be considered a transformation, and thus the latter ECG would be considered a "virtual ECG."

The term "virtual lead angle" refers to an actual angle that is associated with a virtual lead.

Though much of the following discussion is cardiac related, it should be understood that principles related herein are equally applicable to non-cardiac applications. As such it is intended that the scope of the claims of present invention not be so limited, but include any application whereby a physiological signal can be transformed into a vector representation.

Physicians and other medical professionals typically diagnose cardiac pathologies using ECGs rather than the related, and often more diagnostically valuable, VCGs. There may be a number of reasons for this preference, including the relatively simpler nature of the ECG curves, greater familiarity with ECGs, and the typical need for a mathematical transformation to obtain the VCG. Whether viewed or not by the medical professionals, however, VCGs can be highly beneficial when associated with ECG signals. For example, once a VCG has been computed from at least two ECG signals having different recording angles, that VCG can be transformed into a virtual ECG signal representing a virtual lead at any angle. As such, in one embodiment, the virtual ECG signal can be used to replace an ECG signal from a lead that has been lost or altered due to movement or failure of a recording electrode, or is otherwise not available. For example, if ECG signals were recorded from a lead at 0° and a lead at 60°, a VCG could be constructed as described herein. If the lead at 0° is subsequently lost, the VCG can be transformed into a virtual ECG signal at 0°, thus replacing the lost lead. This procedure can be used to maintain consistency in the observed ECG signal over time regardless of the position of the recording electrodes. Also, virtual ECG signals can be obtained at angles for which there are no recording electrodes on the patient. Various situations are contemplated where virtual ECG signals can be constructed at angles having no recording electrodes. For example, in one aspect an electrode may have been removed and replaced in a different location due to skin irritation, physiological noises such as breathing or EMG noise, noise artifacts due to other equipment, etc. A virtual ECG can be constructed at the angle represented by the electrode prior to its removal in order to maintain familiarity for the medical professional. Alternatively, virtual ECG signals can be constructed at angles having no recording electrodes for diagnostic or pathological reasons. This may be useful in examining an injury current or searching for a particular angle-related pathology. For example, the medical professional may utilize a virtual ECG at different angles in order to examine valve leakage, edema, etc.

Accordingly, one aspect of the present invention provides a method of creating a virtual lead associated with an ECG signal. The method can include steps of obtaining a first ECG signal from a first lead having a first angle and a second ECG signal from a second lead having a second angle, where the first lead and the second lead are associated with a subject. The method can further include transforming the first and second ECG signals into a VCG and transforming the VCG into a virtual ECG signal representing a virtual lead having a virtual lead angle. In one aspect, the virtual lead angle can be the same as either the first angle or the second angle. In another aspect, the virtual lead angle can be different from both the first angle and the second angle.

ECG signals can be obtained by electrically associating at least two leads with a subject, with each lead being comprised of at least two recording electrodes. The ECG signal is recorded from the subject via the associated leads. Though an ECG signal can be recorded from a single lead, two leads are utilized in order to calculate the VCG. In other words, ECG signals from at least two leads are generally used in order to generate a VCG representation of the electrical activity of the heart. Also, as is well know in the art, a single electrode can function as an electrode for more than one lead.

As shown in FIG. 1, one common method of recording an ECG signal, as described above, utilizes a three-lead relationship 20. Electric potentials between any two electrodes comprising a lead can be recorded as an ECG. So, for the three-lead example comprising Leads I, II, and III, a recording in Lead II is the sum of the recordings in Leads I and III. These three leads provide the basis for a clockwise polar coordinate system 22 in which angle 0° is along Lead I, and thus Lead I is at 0°, Lead II is at 60°, and Lead III is at 120°. In FIG. 1, Lead I measures electrical potentials between the right arm 24 and the left arm 26, Lead II measures electrical potentials between the right arm and the left leg 28, and Lead III measures electrical potentials between the left arm and the left leg. This configuration should not, however, be seen as limiting the present invention.

The transformation of the ECG signals into a VCG can occur during an overlapping period of time with respect to obtaining of the first and the second electrocardiogram signals. In other words, the transformation can occur concurrently with obtaining the ECG signals. The overlapping period can be completely overlapping, or merely overlapping for a short period of time. The actual transformation of the ECG signals into the VCG may be delayed slightly from the recording step due to the manner in which data is processed in the recording apparatus.

In another aspect, ECG signals can be obtained from a storage location prior to transformation into a VCG. The storage location may include any type of digital or analogue storage known to one skilled in the art, such as, but not limited to, hard disk storage, removable disk storage, tapes, optical disks, flash memory, RAM or other volatile memory, etc. The ECG can be obtained from a workstation, an ECG recording device, a handheld computer, a laptop, a network, a cellular network, or by any other means known to one skilled in the art.

Various methods of transforming ECG signals into a VCG may be contemplated by one skilled in the art, and all are intended to be within the scope of the present invention. The following is an example demonstrating one method of such a transformation. The material described herein is not intended to be limiting, but merely exemplary of one transformation technique. A VCG can be obtained in the following manner by the transformation of at least two ECG signals recorded simultaneously from a pair of leads. The ECG to VCG transformation calculations are presented here for all three lead pair combinations from a common three-lead relationship, but it should be noted that signals from only two leads are required to generate the VCG. Also, for the following, at any time (t), the magnitude (voltage) of the recording for Lead I(t) is defined as LI, the magnitude (voltage) of the recording for Lead II(t) is defined as LII, and the magnitude (voltage) of the recording for Lead III(t) is defined as LIII.

For the Lead I and II combination, the first task is to define the angle ($\theta$) and magnitude (E) of the VCG at time (t), from LI and LII. Since Lead I is at 0° and Lead II is at 60° (see FIG. 1), E is the vector addition of the values along Leads I and II. Assume E is at angle $\theta$. Then:

$$LI = E \cos(\theta) \quad \text{Equation 1}$$

and $$LII = E \cos(60 - \theta) \quad \text{Equation 2}$$

Now, since cos(A-B)=cos(A)cos(B)+sin(A)sin(B), we have $$LII=(E/2)[\cos(\theta)+\sqrt{3}\sin(\theta)] \qquad \text{Equation 3}$$

Combining Equations 1 and 3, we get:

$$LII/LI = (1/2)\left[1 + \sqrt{3}\tan(\theta)\right] \qquad \text{Equation 4}$$

And thus:

$$\theta = \tan^{-1}\left(\frac{2LII - LI}{\sqrt{3}\,LI}\right) \qquad \text{Equation 5}$$

Next calculate the sin(θ) and the cos(θ). Since the hypotenuse of θ is $$\sqrt{[2LII - LI]^2 + \left[\sqrt{3}\,LI\right]^2},$$

or in simplified form:

$$\text{hypotenuse}(\theta) = \sqrt{4LII^2 - 4LI(LII) + 4LI^2} \qquad \text{Equation 6}$$

Then $$\cos(\theta) = \frac{\sqrt{3}\,LI}{2\sqrt{LII^2 - LI(LII) + LI^2}} \qquad \text{Equation 7}$$

And $$\sin(\theta) = \frac{2LII - LI}{2\sqrt{LII^2 - LI(LII) + LI^2}} \qquad \text{Equation 8}$$

From which $$E = \frac{2\sqrt{LII^2 - LI(LII) + LI^2}}{\sqrt{3}} \qquad \text{Equation 9}$$

For the generation of the VCG, the following can be used:
1. The measurements for LI(t) and LII(t) for the two leads.
2. Equation 5 to determine angle θ.
3. Equation 9 to determine the magnitude, E.
4. The value LI is the x-vertex.
5. The y-vertex is computed from Equation 10.

$$y = E\cos(90-\theta) = E\sin(\theta) \qquad \text{Equation 10}$$

Then, for each time (t) sample, an (x,y) vertex is generated, and hence the vectorcardiogram.

For the Lead I and III combination, the first task is to define the angle (θ) and magnitude (E) of the VCG at time (t), from LI and LIII. Since Lead I is at 0° and Lead III is at 120° (see FIG. 1), E is the vector addition of the values along Leads I and III. Assume E is at angle θ. Then:

$$LI = E\cos(\theta) \qquad \text{Equation 11}$$

And $$LIII = E\cos(120-\theta) \qquad \text{Equation 12}$$

Now, since cos(A-B)=cos(A)cos(B)+sin(A)sin(B), we have $$LIII = (E/2)[\sqrt{3}\sin(\theta) - \cos(\theta)] \qquad \text{Equation 13}$$

Combining Equations 11 and 13, we get:

$$LIII/LI = (1/2)\left[\sqrt{3}\tan(\theta) - 1\right] \qquad \text{Equation 14}$$

And thus:

$$\theta = \tan^{-1}\left(\frac{2LIII + LI}{\sqrt{3}\,LI}\right) \qquad \text{Equation 15}$$

Next calculate the sin(θ) and the cos(θ). Since the hypotenuse of θ is $$\sqrt{[2LIII + LI]^2 + \left[\sqrt{3}\,LI\right]^2},$$

or in simplified form:

$$\text{hypotenuse}(\theta) = \sqrt{4LIII^2 + 4LI(LIII) + 4LI^2} \qquad \text{Equation 16}$$

Then $$\cos(\theta) = \frac{\sqrt{3}\,LI}{2\sqrt{LIII^2 + LI(LIII) + LI^2}} \qquad \text{Equation 17}$$

And $$\sin(\theta) = \frac{2LIII - LI}{2\sqrt{LIII^2 + LI(LIII) + LI^2}} \qquad \text{Equation 18}$$

From which $$E = \frac{2\sqrt{LIII^2 + LI(LIII) + LI^2}}{\sqrt{3}} \qquad \text{Equation 19}$$

For the generation of the VCG, the following can be used:
1. The measurements for LI(t) and LIII(t) for the two leads.
2. Equation 15 to determine angle θ.
3. Equation 19 to determine the magnitude, E.
4. The value LI is the x-vertex.
5. The y-vertex is computed from Equation 20.

$$y = E\cos(90-\theta) = E\sin(\theta) \qquad \text{Equation 20}$$

Then, for each time (t) sample, an (x,y) vertex is generated, and hence the vectorcardiogram.

For the Lead II and III combination, the first task is to define the angle (θ) and magnitude (E) of the VCG, at time (t), from LII and LIII. Since Lead II is at 60° and Lead III is at 120° (see FIG. 1), E is the vector addition of the values along Leads II and III. Assume E is at angle θ. Then:

$$LII = E\cos(60-\theta) \qquad \text{Equation 21}$$

And $$LIII = E\cos(120-\theta) \qquad \text{Equation 22}$$

Now, since cos(A-B)=cos(A)cos(B)+sin(A)sin(B), we have $$LII = (E/2)[\cos(\theta) + \sqrt{3}\sin(\theta)] \qquad \text{Equation 23}$$

$$LIII = (E/2)[\sqrt{3}\sin(\theta) - \cos(\theta)] \qquad \text{Equation 24}$$

Combining Equations 23 and 24, we get:

$$LIII/LII = \frac{\sqrt{3}\tan(\theta) - 1}{\sqrt{3}\tan(\theta) + 1}$$ Equation 25

And thus:

$$\theta = \tan^{-1}\left[\frac{LII + LIII}{\sqrt{3}(LII - LIII)}\right]$$ Equation 26

Next calculate the $\sin(\theta)$ and the $\cos(\theta)$. Since the hypotenuse of $\theta$ is $$\sqrt{[LII + LIII]^2 + [\sqrt{3}(LII - LIII)]^2},$$

or in simplified form:

$$\text{hypotenuse}(\theta) = \sqrt{4LII^2 - 4LII(LIII) + 4LIII^2}$$ Equation 27

Then $$\cos(\theta) = \frac{\sqrt{3}(LII - LIII)}{2\sqrt{LII^2 - LII(LIII) + LIII^2}}$$ Equation 28

And $$\sin(\theta) = \frac{LII + LIII}{2\sqrt{LII^2 - LII(LIII) + LIII^2}}$$ Equation 29

From which $$E = \frac{2\sqrt{LII^2 - LII(LIII) + LIII^2}}{\sqrt{3}}$$ Equation 30

For the generation of the VCG, the following can be used:
1. The measurements for LII(t) and LIII(t) for the two leads.
2. Equation 26 to determine angle $\theta$.
3. Equation 30 to determine the magnitude, E.
4. The value x-vertex is computed from Equation 31.

$$x = E\cos(\theta)$$ Equation 31

5. The y-vertex is computed from Equation 32.

$$y = E\cos(90-\theta) = E\sin(\theta)$$ Equation 32

Then, for each time (t) sample, an (x,y) vertex is generated, and hence the VCG.

Once the ECGs have been transformed into a VCG representation, a virtual ECG can be generated therefrom. The virtual ECG can be used to replace any existing lead, whether that lead was utilized to construct the VCG or not. Various situations may facilitate the generation of a virtual ECG from the VCG representation in order to replace an existing lead, including, without limitation, the need to regenerate an ECG recording from a lead that has been lost, degraded, or altered in some way. The construction of the virtual ECG can occur prior to or following such loss, degradation, or alteration of a lead. In addition to exhibiting very similar shape characteristics, the virtual peak magnitude of the virtual ECG can be altered to approximate or equal the peak magnitude of the ECG recording from the lead having the same angle as the virtual ECG.

A virtual ECG can be generated from the VCG for any lead associated with the subject. As an example, ECGs for Leads I, II, and III, can be generated by calculating the magnitude (voltage) of the ECG for that lead at any time (t), using the magnitude (E) and the angle ($\theta$) from the VCG in each of Equations 33, 34, and 35, respectively.

$$LI = E\cos(\theta)$$ Equation 33

$$LII = E\cos(60-\theta)$$ Equation 34

$$LIII = E\cos(120-\theta)$$ Equation 35

A virtual ECG representation having a recording angle that does not correspond to one of the physical leads may be utilized for various diagnostic and treatment purposes. This may be beneficial when examining an injury current at an angle not represented by one of the associated leads, when recording from a particular angle for diagnostic purposes, etc. A virtual ECG (LV) can be constructed from a VCG at any desired angle ($\sigma$) by calculating the magnitude (voltage) of the ECG for that lead at any time (t), using the magnitude (E) and the angle ($\theta$) from the VCG in Equation 36.

$$LV = E\cos(\sigma-\theta)$$ Equation 36

Accordingly, in one aspect, a method of diagnosing and/or monitoring a cardiac condition is provided. The method can include steps of obtaining a first ECG signal from a first lead having a first angle and a second ECG signal from a second lead having a second angle. In this case the first lead and the second lead would be, of course, associated with a subject. The method can also include steps of determining a monitoring angle, transforming the first and second ECG signals into a VCG representation, and transforming the VCG representation into a virtual ECG signal representing a virtual lead having the monitoring angle.

It should be noted that the monitoring angle can be any angle. In one aspect, the monitoring angle can be different from both the first angle and the second angle. In another aspect, the monitoring angle can be the same as either the first angle or the second angle. As has been discussed herein, determining the monitoring angle can occur for a variety of reasons, such as the need to monitor an injury current, or for monitoring a subject at a particular monitoring angle for diagnostic purposes. Accordingly, in one aspect the monitoring angle can correspond to the angle of an injury current.

Various factors may influence the accuracy of the virtual ECG reconstruction. One such factor can include the selection of leads from which the VCG will be constructed. Given the differential placement of the leads on the body, specific leads may produce signals of varying quality. Factors determining the differential quality that may exist between leads can include local motion, endogenous biological signals such as muscular noise, line noise, etc. It can be beneficial to select a pair of leads that provides an acceptable level of signal quality for transforming the ECG into the VCG. In many cases it may be desirable to select the pair of leads that has a higher level of signal quality than each of the other combinations of pairs of leads, i.e., the pair with the highest level of signal quality. Because many of the types of noise artifacts that may be present in an ECG can be linearly independent and independently identifiable, lead selection can be based on any number of criteria, one of which may include a weighted combination of the prevalence of each distinct noise artifact.

In one aspect, a simpler method of selection of a pair of leads can include estimating what percent of the signal suffers from one or more of the distinct noise artifact(s). Simply taking the signal variance may not be sufficient, for example, because a signal that is fully saturated only on one side of the range will have zero variance, but also zero signal. In such a situation, breaking up the waveform into reasonably sized time windows, e.g., 1000 msec, and assessing whether noise is present may prove beneficial. For example, each time window containing a particular type of noise artifact can be tagged with a "1." Those signals with noise present will have a higher variance than a "cleaner" signal. As such, leads with a lower variance can be preferentially selected.

In an even simpler aspect, the leads can be prioritized and the best pair of leads selected based only on breathing/motion signal artifacts using the variance methods as described herein. This is due to an assumption that many common signal artifacts can be discounted due to their nature. For example, it can be assumed that DC drift may be irrelevant, because a medical diagnosis does not depend on the DC value and DC values disappear from the VCG anyway. Also, it can be assumed that saturation does not occur because the gain of the recording instrument is not set high enough. Additionally, many common signal artifacts can be removed, further justifying selecting a pair of leads based primarily on breathing/motion artifacts. For example, power line noise can be removed with a 50 or 60 Hz notch filter, depending on the frequency of the noise. DC drift can be removed by applying a high-pass filter to the signal. Segments of the signal having saturation noise artifacts can be discarded as unreliable data.

It can be beneficial to filter various signal artifacts from the VCGs prior to generating the virtual ECG. Such filtering can allow the generation of virtual ECGs with fewer signal artifacts than the original ECG signals. Because VCGs have smoother curves than ECGs, noise artifact removal via filtering a VCG is much more straightforward. Following filtering, the VCG can be transformed to a virtual ECG signal in order to provide physicians and other medical professionals with cardiac data in a more familiar form, to replace a lost or degraded physical lead, or to record from an angle at which there are no physical leads present. Such filtering can result in a much improved virtual ECG signal.

In one aspect of the present invention, filtering the VCG may include reducing a VCG signal artifact. Various types of artifacts may be present in the ECG signals and the resulting VCG, including electrical noise, thermal noise, movement artifacts, breathing artifacts, and combinations thereof. The following is a description of a few types of noise artifacts that are often present. It should be noted, however, that any type of noise capable of being filtered from the signal is considered to be within the scope of the present invention.

One common type of signal artifact is power line noise. This type of noise is a result of the AC frequency of the power lines being picked up by the recording leads. The signal is about 60 Hz in the United States, and about 50 Hz in Europe. Any means of performing a time-to-frequency transformation can be used to find the line frequency component, including the discrete Fourier transform (DFT), which is well known to one skilled in the art. The 50/60 Hz component can be directly assessed by locating a 50 or 60 Hz peak in the frequency spectrum. In the attenuation of power line noise, it is useful to note that although the presence of a 50/60 Hz peak may originate from a biological signal, it will not be of a constant phase relationship when viewed in the VCG domain, while a 50/60 Hz peak from power line noise will be of a constant phase relationship. As such, identification of power line noise may be accomplished by examination of frequency and phase relations. As an aside, if performance is restricted, the 50/60 Hz artifacts can be processed with breathing/motion artifact filtering, as discussed herein.

Another common type of signal artifact is referred to as DC shift or DC drift. Because different electrode combinations, and thus different leads, will have different relative skin-electrode offset potentials, the mean voltage on the leads can differ. When the mean value is significantly different from zero and/or the mean value of a clean signal, the lead is said to have a DC drift. For simplicity, DC drift is the magnitude of the mean value of the voltage on any particular lead. In order to detect DC drift, the mean value of a signal is measured over a reasonable time period, e.g., 1000 msec. If the measured value is greater than a small percentage of the peak-to-peak signal range (highest voltage to lowest voltage over the interval), then DC drift is present. The severity of the DC drift can be estimated from the equation: |mean value of voltage|/(+ supply voltage).

Yet another common type of signal artifact is referred to as saturation. Sensors and analogue-to-digital converters have a range of values to which they typically respond, which is often determined by the supply voltage, e.g. +/−1.5. Sampled signal values at either end of this range are considered "saturated" because their actual values are outside of the range of the signal recording equipment. These saturated signals appear to have portions that are "clipped" or "cropped" off at the upper and/or lower range. Saturation can be assessed by looking for signals that: 1) are within 10% of the +/− supply voltage (postamplification); 2) are consistent from one sample to the next; and 3) have a low variance. It should be noted that the voltage at saturation will rarely be exactly the same as the supply voltage. In some cases, 5-10% variation in the actual +/− supply voltage will be commonplace, and so detection of saturation must take this into account.

One of the most significant sources of signal artifacts results from breathing, muscular movements, and other motion artifacts of the patient during cardiac signal recording. Breathing typically occurs between 10-20 times per minute, and thus has a frequency bandwidth in the range of 0.17-0.33 Hz. Muscular (electromyogram, or EMG) and motion artifacts have a higher frequency content than breathing artifacts, and tend to spread throughout much of the measured frequency spectrum. A variety of techniques for assessing breathing/motion artifacts can be utilized in the present invention. The methods described hereafter are not intended to be limiting, and may also be utilized to reduce any type of periodic signal artifact. One method is the use of a simple variance. The variance is the sum of the squared error from the mean of the signal, divided by the number of samples. Signals may be used containing DC drift, although saturated signals may be eliminated. Since this method does not distinguish between one part of the time window and another, a signal with an episode of very high noise will have a similar variance to a signal with moderate noise throughout the time window.

Another method of assessing breathing/motion artifacts examines the summed score of the sub-interval variance. In this method, the time window, e.g., 1000 msec, is divided into sub-intervals, e.g., 25 msec, and the variance assessed. Variance above the normal 50% peak-to-peak range of the biological signal is considered "high", and scored as one point for every multiple it is of the 50% peak-to-peak range. In a normal ECG, only the QRS complex will cause a point to be recorded. Given average heart rates of approximately 1-3 beats per second, the summed score will typically be from 1-3. Breathing/motion artifacts will cause this score to climb above 10, thus indicating the presence of cyclic signal noise.

Yet another method of assessing breathing/motion artifacts examines the percent of sub-intervals with high variance. In this method, a time window is divided into sub-intervals as described above. In this case, the number of sub-intervals with a high variance is divided by the number of sub-intervals.

This corrects for differences in the absolute value of the QRS complex, and provides normalization across leads of differing orientation.

Any means of filtering a signal artifact from a VCG should be considered within the scope of the present invention. As such, the filtering examples described herein are merely illustrative, and are not intended to be limiting. For example, the current VCG may be filtered by using a previous or other VCG as a template for the current VCG, whereby the current VCG is fit to the template by eliminating extreme outliers until a stable smooth curve is obtained. One method for accomplishing this is through recursive curve fitting (nonlinear regression).

The VCG can also be filtered by determining the variability in the rate of change in the VCG data, including both the magnitude and direction, especially during the PQ, ST, and TP intervals of the VCG, to determine the type of noise present. Noise information can be used to clean up the P, QRS, and/or T loops. In other words, the VCG can be filtered specifically for the type of noise identified.

Noise artifacts can also be eliminated by checking for large instantaneous changes in the VCG magnitude and/or angle. Since the VCG is normally smooth, even under a variety of cardiac anomalies such as flutter and fibrillation, large instantaneous changes can be discarded and the remaining points in the curve can be fitted with interpolation, e.g., cubic spline, etc., to generate a noise free curve approximation. In one aspect, spikes in the VCG which result in instantaneous deviations of more than about 10% of the mean of the major/minor axes of the loop can be discarded. Also, iterative methods can be used. The VCG can also be filtered by replacing each value of the VCG curve with the moving average of the value and its surrounding values. Note that in healthy patients, the angle of the VCG is monotonically changing throughout a vector loop. Also, in general, it forms a convex loop. These are advantageous for noise reduction, compared to the "discontinuous" signals in the ECG.

The principles outlined in the various embodiments of the present invention apply not only to cardiac-related physiology, but also to any physiological signal that can be transformed into a vector representation. Accordingly, in one embodiment, a method of creating a virtual lead associated with a physiological recording is provided. The method can include steps of obtaining a first physiological signal from a first lead having a first angle and a second physiological signal from a second lead having a second angle. The first and second leads are, of course, associated with a subject. The method can also include transforming the first and second physiological signals into a vector representation of the first and second physiological signals and transforming the vector representation to a virtual physiological signal representing a virtual lead having a virtual lead angle. The virtual lead angle can be the same as either the first angle or the second angle, or the virtual lead angle can be different from both the first and second angles.

Various physiological signals are contemplated that can be recorded and transformed into vector representations. Any physiological signal that can undergo such a transformation is considered to be within the scope of the present invention. In one specific embodiment, the first and second physiological signals can be ECG signals. In another embodiment, the first and second physiological signals can be EMG signals. In yet another embodiment, the first and second physiological signals can be EEG signals. In a further embodiment, the first and second physiological signals can be blood pressure signals.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications may be made without departing from the principles and concepts set forth herein.

What is claimed is:

1. A method of creating a virtual lead associated with an electrocardiogram signal, comprising the steps of:
    obtaining a first electrocardiogram signal from a first lead having a first angle and a second electrocardiogram signal from a second lead having a second angle, the first lead and the second lead being associated with a subject;
    transforming the first and second electrocardiogram signals into a vectorcardiogram;
    moving average filtering the vectorcardiogram in polar coordinate space to reduce signal artifacts prior to transforming the vectorcardiogram into a virtual electrocardiogram signal; and
    transforming the vectorcardiogram into the virtual electrocardiogram signal representing a virtual lead having a virtual lead angle.

2. The method of claim 1, wherein the step of transforming the vectorcardiogram occurs during an overlapping period of time with respect to the step of obtaining the first and the second electrocardiogram signals.

3. The method of claim 1, wherein the virtual lead angle is the same as either the first angle or the second angle.

4. The method of claim 1, wherein the virtual lead angle is different from both the first angle and the second angle.

5. The method of claim 1, wherein the step of transforming the vectorcardiogram to the virtual electrocardiogram signal representing the virtual lead further includes a step of altering a virtual peak magnitude of the virtual electrocardiogram signal to approximate or equal a peak magnitude of either the first electrocardiogram signal or the second electrocardiogram signal.

6. The method of claim 1, wherein either of the first or second electrocardiogram signals has been lost, degraded, or altered prior to the step of transforming the vectorcardiogram into the virtual electrocardiogram signal.

7. The method of claim 1, wherein the signal artifact is a member selected from the group consisting of electrical noise, thermal noise, movement artifacts, breathing artifacts, and combinations thereof.

8. A method of diagnosing and/or monitoring a cardiac condition, comprising:
    obtaining a first electrocardiogram signal from a first lead having a first angle and a second electrocardiogram signal from a second lead having a second angle, the first lead and the second lead being associated with a subject;
    determining a monitoring angle;
    transforming the first and second electrocardiogram signals into a vectorcardiogram;
    moving average filtering the vectorcardiogram in polar coordinate space to reduce signal artifacts prior to transforming the vectorcardiogram into a virtual electrocardiogram signal; and transforming the vectorcardiogram into the virtual electrocardiogram signal representing a virtual lead having the monitoring angle.

9. The method of claim 8, wherein the monitoring angle corresponds to an injury current angle.

10. The method of claim 8, wherein the monitoring angle is different from both the first angle and the second angle.

11. The method of claim 8, wherein the monitoring angle is the same as either the first angle or the second angle.

12. A method of creating a virtual lead associated with a physiological recording, comprising:
    obtaining a first physiological signal from a first lead having a first angle and a second physiological signal from a second lead having a second angle, the first lead and the second lead being associated with a subject;
    transforming the first and second physiological signals into a vector representation of the first and second physiological signals;
    moving average filtering the vector representation of the first and second physiological signals in polar coordinate space to reduce signal artifacts prior to transforming the vector representation to a virtual physiological signal; and
    transforming the vector representation to the virtual physiological signal representing a virtual lead having a virtual lead angle.

13. The method of claim 12, wherein the step of transforming the vector representation occurs during an overlapping period of time with respect to the step of obtaining the first and the second physiological signals.

14. The method of claim 12, wherein the virtual lead angle is the same as either the first angle or the second angle.

15. The method of claim 12, wherein the virtual lead angle is different from both the first angle and the second angle.

16. The method of claim 12, wherein the step of transforming the vector representation to the virtual physiological signal representing the virtual lead further includes a step of altering a virtual peak magnitude of the virtual physiological signal to approximate a peak magnitude of either the first physiological signal or the second physiological signal.

17. The method of claim 16, wherein the peak magnitude is obtained from either the first or second physiological signals.

18. The method of claim 12, wherein either of the first or second physiological signals have been lost, degraded, or altered prior to the step of transforming the vector representation.

19. The method of claim 12, wherein the signal artifact is a member selected from the group consisting of electrical noise, thermal noise, movement artifacts, breathing artifacts, and combinations thereof.

20. The method of claim 12, wherein the first and second physiological signals are electrocardiogram signals.

21. The method of claim 12, wherein the first and second physiological signals are electromyogram signals.

22. The method of claim 12, wherein the first and second physiological signals are electroencephalogram signals.

23. The method of claim 12, wherein the first and second physiological signals are blood pressure signals.

* * * * *